US010758186B2

(12) United States Patent
Yu et al.

(10) Patent No.: US 10,758,186 B2
(45) Date of Patent: Sep. 1, 2020

(54) PHYSIOLOGICAL SIGN INFORMATION ACQUISITION METHOD AND SYSTEM

(71) Applicant: VITA-COURSE TECHNOLOGIES CO., LTD., ShenZhen (CN)

(72) Inventors: Jiao Yu, ShenZhen (CN); Jiwei Zhao, ShenZhen (CN); Zhiyong Wang, ShenZhen (CN)

(73) Assignee: VITA-COURSE TECHNOLOGIES CO., LTD., Shenzhen (CN)

( * ) Notice: Subject to any disclaimer, the term of this patent is extended or adjusted under 35 U.S.C. 154(b) by 385 days.

(21) Appl. No.: 15/567,974

(22) PCT Filed: Apr. 20, 2015

(86) PCT No.: PCT/CN2015/077026
§ 371 (c)(1),
(2) Date: Oct. 20, 2017

(87) PCT Pub. No.: WO2016/168980
PCT Pub. Date: Oct. 27, 2016

(65) Prior Publication Data
US 2018/0116597 A1    May 3, 2018

(51) Int. Cl.
*A61B 5/00* (2006.01)
*A61B 5/04* (2006.01)
(Continued)

(52) U.S. Cl.
CPC .......... *A61B 5/7207* (2013.01); *A61B 5/0064* (2013.01); *A61B 5/0245* (2013.01);
(Continued)

(58) Field of Classification Search
CPC . A61B 5/7207; A61B 5/0064; A61B 5/02416; A61B 5/0245; A61B 5/04012;
(Continued)

(56) References Cited

U.S. PATENT DOCUMENTS

| 8,632,465 B1* | 1/2014 | Brockway | H03H 17/0248 600/300 |
| 2015/0094552 A1* | 4/2015 | Golda | A61B 5/04325 600/336 |
| 2015/0283387 A1 | 10/2015 | Sun et al. | |

FOREIGN PATENT DOCUMENTS

| CN | 101953682 A | 1/2011 |
| CN | 102988041 A | 3/2013 |

(Continued)

OTHER PUBLICATIONS

International Search Report in PCT/CN2015/077026 dated Jan. 21, 2016, 6 pages.

*Primary Examiner* — Erin M Piateski
(74) *Attorney, Agent, or Firm* — Metis IP LLC

(57) ABSTRACT

The present disclosure relates to a vital sign extraction method and system. The system comprises a receiving module for receiving at least one type of physiological information; a feature extraction module configured to extract a first feature and a second feature of the physiological information by using a first technique and a second technique; a processing module for performing a matching calculation on the first feature and the second feature, marking matching results, and identifying a noise result of the physiological information based on the matching results; and a calculation module for calculating a physiological sign of a living body.

14 Claims, 8 Drawing Sheets

(51) Int. Cl.
    *A61B 5/0402*    (2006.01)
    *A61B 5/0245*    (2006.01)
    *A61B 5/024*     (2006.01)
    *A61B 5/0205*    (2006.01)
    *A61B 5/01*      (2006.01)
    *A61B 5/021*     (2006.01)
    *A61B 5/1455*    (2006.01)

(52) U.S. Cl.
    CPC ........ *A61B 5/02416* (2013.01); *A61B 5/0402* (2013.01); *A61B 5/04012* (2013.01); *A61B 5/7246* (2013.01); *A61B 5/01* (2013.01); *A61B 5/021* (2013.01); *A61B 5/02055* (2013.01); *A61B 5/02405* (2013.01); *A61B 5/14551* (2013.01); *A61B 2560/0214* (2013.01)

(58) Field of Classification Search
    CPC ....... A61B 5/0402; A61B 5/7246; A61B 5/01; A61B 5/021; A61B 5/02045; A61B 5/14551; A61B 2560/0214
    USPC .......................................................... 600/513
    See application file for complete search history.

(56)         References Cited

FOREIGN PATENT DOCUMENTS

| CN | 103083013 A | 5/2013 |
| CN | 104102915 A | 10/2014 |
| CN | 104182625 A | 12/2014 |

\* cited by examiner

PHYSIOLOGICAL SIGN INFORMATION ACQUISITION METHOD AND SYSTEM

CROSS-REFERENCE TO RELATED APPLICATIONS

The present application is a U.S. national stage under 35 U.S.C. § 371 of International Application No. PCT/CN2015/077026, filed on Apr. 20, 2015, designating the United States of America, which is related to a PCT application entitled "SYSTEMS AND METHODS FOR PHYSIOLOGICAL SIGN ANALYSIS" filed on Apr. 20, 2015, the entire contents of which are hereby incorporated by reference.

TECHNICAL FIELD

The present disclosure relates to systems and methods for acquiring, processing, extracting, and analyzing physiological sign information.

BACKGROUND

A living body produces and releases a lot of life information all the time. The life information may be summarized into two categories: chemical information (chemical components that constitute the living body and information relating to its changes) and physical information (shapes, locations, relative relationships of organs in the living body, and force, heat, sound, light, and other related information generated by movement of the living body). A circulatory system formed by Heart and vessels of some animals may constitute a blood circulation and may be one of the most important organs and components for the animals. The chemical information and physical information of a cardiovascular system contains a large amount of information about health of the animals. Among them, one of the main techniques applied to diagnosing heart conditions and performances is electrocardiogram (ECG). The ECG records the surface potential difference produced during the beating of the heart. In 1903, Einthoven, a professor of physiology in Leiden University in the Netherlands, measured the ECG using a string electrometer manual. In addition, an animal body pulse system is an important component of the cardiovascular system and an important way to transport nutrients and transfer energy. A pulse comes directly from the heart and is a fluctuation caused by the contraction of the heart. A left ventricle injects blood into an aorta through an aortic valve, causing a pulsation of flow, pressure, and diameter in the arterial tree. One of the important life information generated by the pulse system is photoplethysmography (PPG). The propagation characteristics of the PPG are closely related to the changes of mechanical parameters in the cardiovascular system and the PPG includes a lot of physiological information of the animal body. In 1860, Vierordt, a Frenchman, developed the first spring lever-type pulse tracer to obtain a pulse wave waveform.

The measurement of the PPG or the measurement of the ECG may be effected by noises, artifacts, and data loss, which may result in a wrong analysis result. Generally, the following common noise interference may exist in collected signals: baseline drift, power frequency interference, electromyographical interference, and motion/vibration interference. The baseline drift is caused by a poor contact of clicks and impedance changes on the electrode-skin interface of a subject. The baseline drift is a low frequency interference signal and the frequency is generally less than 1 Hz. The power frequency interference is generated because that a distribution capacitance on human body and a lead loop of click electrode are affected by an alternating current and a magnetic field. The frequency of the power frequency interference is 50 Hz frequency and its harmonics. The electromyographical interference is caused by body jitter and muscle tension. The frequency of the electromyographical interference is relatively large. The motion/vibration interference may refer to that during the signal input process, a signal generator (e.g., a transmission distance of a light source, a transmission angle of the light source) may change due to movement or vibration of the subject, the light source, or the sensor, and therefore, the signal characteristics are affected and the signal may be disturbed, distorted, or submerged.

SUMMARY

In the present disclosure, a system may be disclosed. The system may comprise: a receiving module configured to receive at least one type of physiological information; a processing module including a feature extraction module, a matching operation module, and a calculation module. The feature extraction module may be configured to process the physiological information by a first technique and a second technique respectively to generate a first feature and a second feature, the first technique being different from the second technique. The matching operation module may be configured to perform a matching operation on the first feature and the second feature, and mark matching results. The calculation module may be configured to calculate a physiological sign of a human body. The processing module may include a preprocessing module.

In some embodiments, the physiological information received by the receiving module may include at least one of electrocardiogram information or pulse information.

In some embodiments, the first technique may include a peak detection algorithm, and the second technique may include a PPG algorithm or an ECG algorithm. The PPG algorithm and the ECG algorithm may include but not be limited to one or more methods, such as a threshold method, a syntactic pattern recognition, a Gaussian function decomposition method, a wavelet transformation, a HTT method, a QRS wave detection algorithm, a local peak detection algorithm, a peak detection algorithm, etc. Similarly, the ECG algorithm may refer to any method aimed at obtaining the ECG results.

In some embodiments, the matching operation module may mark a peak result that is not matched as a noise peak.

In some embodiments, the operations to identify the noise result performed by the matching operation module may include: (1) calculating noise ratios; (2) if a number of noise peaks with noise ratios not less than 1 is greater than half of a number of waves identified based on an algorithm, or (3) if a number of noise peaks with noise ratios not less than 0.75 is greater than 0.75 times of the number of the waves identified based on the algorithm, or (4) if a number of noise peaks with noise ratios not less than 0.5 is greater than the number of the waves identified based on the algorithm, determining that the physiological information includes noise.

In some embodiments, the waves identified based on the algorithm may be waves identified based on a PPG algorithm or an ECG algorithm.

In some embodiments, the calculation module may be configured to calculate at least one physiological sign of a heart rate, a blood pressure, oxygen saturation, a body temperature, an HRV, or a PR value.

DETAILED DESCRIPTION

Figure 1:
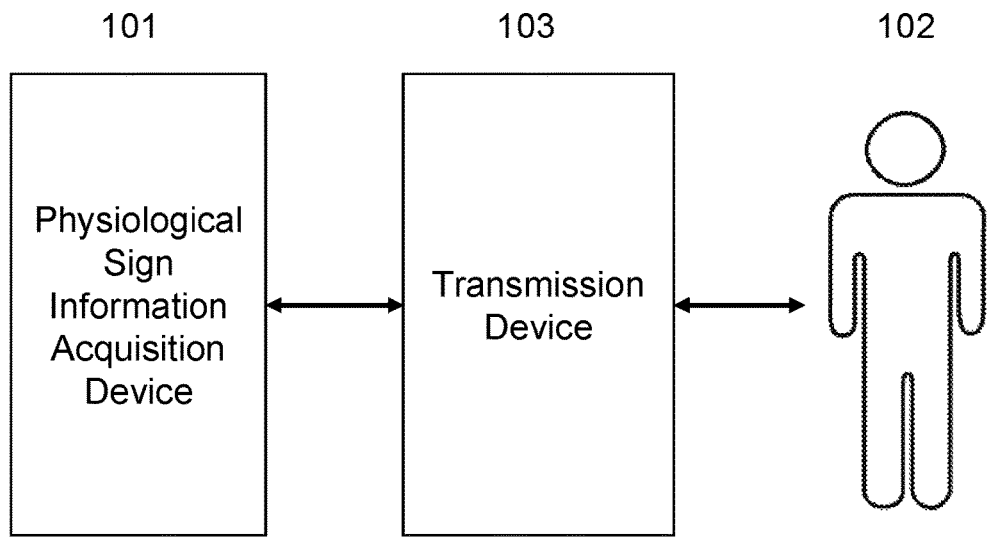
FIG. 1 is an application scenario diagram illustrating a physiological sign information acquisition system in the present disclosure.

In order to illustrate the technical solution of embodiments of the present disclosure, drawings to be used in the description of the embodiments will be briefly described below. Obviously, the drawings in the following description are merely some embodiments of the disclosure, and are not intended to limit the scope of application of the present disclosure. To those skilled in the art, the present disclosure may be applied to other similar scenes according to these drawings without making creative efforts.

The physiological sign information acquisition system in the present disclosure may be applied to a variety of fields including but not limited to care (including but not limited to elderly care, middle-aged care, youth and child care, etc.), medical diagnosis (including but not limited to ECG diagnosis, pulse diagnosis, blood oxygen diagnosis, etc.), sports monitoring (including but not limited to long-distance running, sprinting and middle-distance running, sprinting, cycling, rowing, archery, horse riding, swimming, mountain climbing, etc.), hospital care (including but not limited to monitoring critically sick patients, monitoring patients with genetic disease, monitoring emergency patients), pet care (critically sick pet care, newborn pet care, home pet care), etc.

The physiological information acquisition system may acquire one or more types of physiological information of a living body, such as a pulse, electro cardio, body temperature, and physical, chemical, and biological information related to the living body. The physiological information acquisition system may include a receiving module for receiving one or more types of the physiological information. The physiological information acquisition system may include a processing module. The processing module may include a preprocessing module, a feature extraction module, a matching operation module, and a calculation module. The preprocessing module may preprocess the physiological information. The feature extraction module may process the preprocessed physiological information using a first technique and a second technique respectively to obtain a first feature and a second feature. The matching operation module may perform a matching operation on the first feature and the second feature, mark matching results and identify a noise result of the physiological information. The calculation module may calculate a physiological sign of a human body. The I/O module may output and display the physiological sign. The system may effectively detect noises existing in the received physiological information data with a small amount of calculation. The system may match and calibrate the noises correspondingly. The system may be easily applied to a portable device or a wearable device. The system may continuously monitor the physiological information of the living body in real time (or in non-real time) and transmit monitoring results to external devices (including but not limited to a storage device or a cloud server). For example, the system may continuously monitor the physiological sign of the user over a random period of time, such as several minutes, several hours, several days, or several months, or may continuously monitor the physiological sign of the user at regular intervals. The system may display physiological sign conditions of the monitored living body in real time (and in non-real time), such as pulse, blood pressure, blood oxygen concentration, and provide the physiological information data to a related remote third party, such as a hospital, a nursing institution, or associated people. For example, the user may use this system at home. The physiological sign condition or physiological information data of the user monitored by this system may be provided to a remote hospital, a remote care institution, associated people, etc. A part or all of the physiological sign conditions or physiological information data of the user may also be stored in a local storage device or a remote storage device. The above transmission mode of the physiological information data may be wired or wireless.

The above description of the application filed is merely provided for illustration purposes and should not be considered as the only executable embodiment. For persons having ordinary skills in the art, after understanding the basic principles of the physiological information extraction method and system, may make multiple variations and modifications in the form and details of the application field without departing from the principles of the present disclosure. However, those variations and modifications are within the scope of the present disclosure.

FIG. 1 shows an application scenario diagram of the physiological information acquisition system. The system may include but not limited to a physiological sign information acquisition device 101, a living body 102, and a transmission device 103. The physiological sign information acquisition device 101 may acquire, process, extract, and/or analyze physiological information from the living body 102. The living body 102 may include but not limited to a human body, and other living bodies such as animals and plants that include physiological information may be included in the living body 102, and the living body 102 may not limited to a single living body. The physiological information may include but not limited to physical, chemical, and biological information, such as body temperature, heart rate, pulse, brain wave, ultra-low frequency radio wave issued by the human body, breathing, ECG, musculoskeletal status, organ morphology, organ location, organ status, fat, blood oxygen, blood sugar, platelet content, and the amount of various components in the blood. The transmission system 103 may transmit the physiological information of the living body 102 to the physiological sign information acquisition device 101. The signal transmitted by the transmission device 103 to the physiological sign information acquisition device 101 may be analog or digital, and may be in real time or in non-real time. The transmission device 103 may include but not limited to an embedded device such as a sensor, a processor, a microcontroller, and an ARM, and an electronic, mechanical, physical, chemical device such as an analyzer and a detector. A transmission mode of the transmission device 103 may include a wireless mode including but not limited to a radar, an infrared, a Bluetooth, or a wired mode including but not limited to a cable, an optical fiber. The transmission device 103 may be applied for a specific living body, a plurality of specific living bodies, a group of living bodies, living bodies with a specific type, or living bodies with multiple types. The transmission device 103 may also include a central database. The physiological sign information acquisition device 101 may collect the physiological information directly or indirectly. The collected physiological information may be transmitted to the physiological sign information acquisition device 101 in real time directly by the transmission device 103, or may be transmitted in batches to the physiological sign information acquisition device 101 by the transmission device 103. The physiological sign information acquisition device 101 may or may not process the physiological information, or may store the physiological information. The physiological information of the living body 102 may be acquired by a heart rate collection device, an electrocardiogram detector, a pulse wave detector, a brain wave detector, a vital signal detection device, a breathing tester, a portable monitoring device, a miniaturization device, a non-contact monitoring device, etc. The physiological information of the living body 102 may also be acquired by a wearable intelligent or non-intelligent body temperature monitor, a wrist-type electronic sphygmomanometer, a heart detector, a blood glucose meter, a wrist pulse monitor, an environmental pollution monitoring mask, an intelligent or non-intelligent bracelet, an intelligent or non-intelligent watch, an intelligent or non-intelligent neck ring, etc. The above description of the application scenario of the physiological sign information acquisition system is merely provided for illustration purposes, and should not be considered as the only executable embodiment. For persons having ordinary skills in the art, after understanding the principles of the present disclosure, may make multiple variations and modifications in the form and details of the application of the physiological sign acquisition system without departing from the principles of the present disclosure. However, those variations and modifications are within the scope of the claims of the present disclosure. For example, the various types of physiological information collected from the living body 102 may be directly transmitted to the physiological sign information acquisition device 101 without the transmission device 103. The physiological sign information acquisition device 101 may also simultaneously acquire a variety of different types of information from a plurality of living bodies 102 to perform comprehensive process. Those variations and modifications are within the scope of the claims of the present disclosure.

Figure 2:
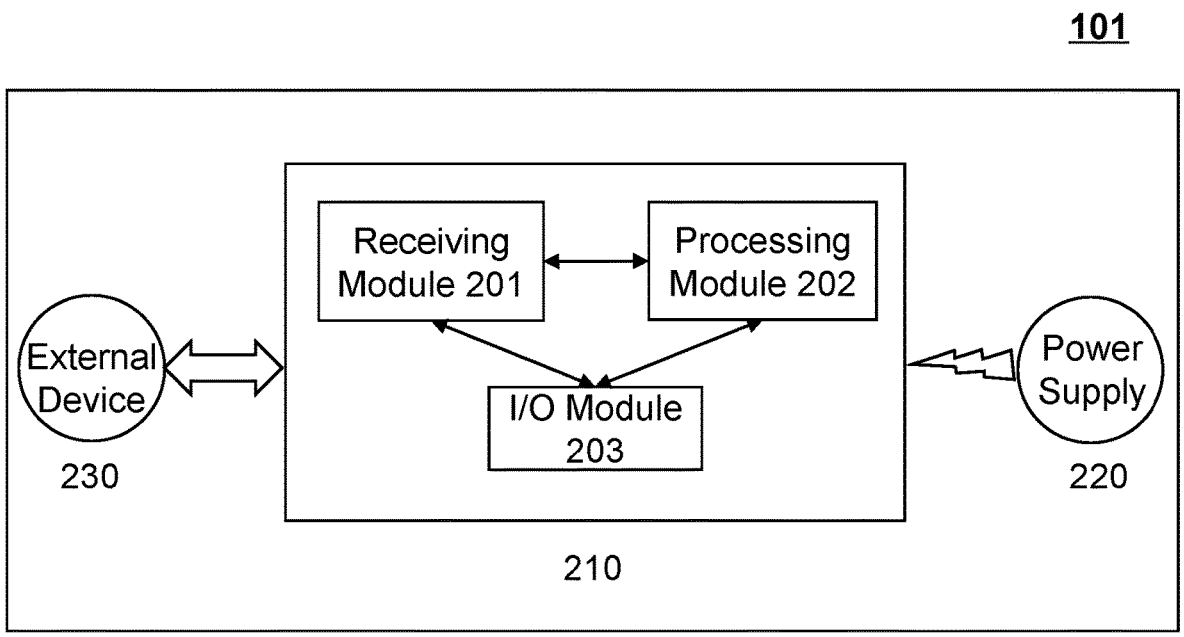
FIG. 2 is a schematic diagram illustrating a physiological sign information acquisition device in the present disclosure.

FIG. 2 shows a schematic diagram of the physiological sign information acquisition device 101. The physiological sign information acquisition device 101 may include but not limited to one or more components 210, one or more power supplies 220, one or more external devices 230, etc. The component 210 may include but not limited to a receiving module 201, a processing module 202, and an I/O module 203. The receiving module 201 may be used to receive the collected physiological information. The receiving module 201 may receive the physiological information in a wired or a wireless mode, or may directly collect the physiological information. The receiving module 201 may be distributed in the physiological sign information acquisition device 101 together with other modules, or may be separated from the physiological sign information acquisition device 101 as an independent component. The receiving module 201 may be a local component or a remote component. It should be noted that the receiving module 201 is not limited to the above-mentioned manners, and manners in which the physiological information can be acquired are within the scope of the present disclosure. The processing module 202 may be mainly used to calculate the physiological information and perform main logical determination. The processing module 202 may be centralized or distributed, and may be local or remote. The I/O module 203 may be used to output or display the physiological information. The I/O module 203 may include but not limited to a display module (not shown), and the display module may display information including but not limited to chart symbols, liquid crystals, vibrations, numeric values, characters, any symbol of a specific semantics, or the like, or a combination thereof. The I/O module 203 may not include the display module but transmit the information to other devices via a wired mode or a wireless node, wherein the other devices may be local or remote.

The power supply 220 may generally refer to different embodiments capable of providing electrical energy. The types of power supplies described below may be only a part of applicable embodiments, but may not include all embodiments that may be applied to the physiological sign information acquisition system. The power supply may include but not limited to an external power supply, an internal battery, or a built-in power generation device of the physiological sign information acquisition system. The external alternating current power supply may include but not limited to a household or an industrial alternating current power supply. Further, different countries or regions may have different requirements for the voltage and frequency of the household alternating current, such as but not limited to: 120V and 60 Hz in the United States and Canada, 220V~240V and 50 Hz in most of the European countries, 230V or 240V and 50 Hz in Australia and New Zealand, 220V and 50 Hz in Argentina and Chile, 110V or 220V and 60 Hz in Brazil, 220V and 50 Hz in most areas of Egypt, South Africa, and Morocco, 127V or 220V and 60 Hz in Saudi Arabia, 230 V and 50 Hz in Turkey, 100V and 50 Hz (east) or 60 Hz (west) in Japan, 220V and 50 Hz in Mainland China, the Hong Kong Special Administrative Region, and the Macao Special Administrative Region, 220V and 60 Hz in South Korea, and 110V and 60 Hz in China Taiwan. Further, the physiological sign information acquisition system may be connected to the household alternating current through an internal wire or through a standard plug. The connection between the system and the household alternating current may refer to but not limited to the following standards: United States standards UL 244A, UL514A, UL514B, UL514C, UL514D, CSA C22.2 No. 177, NFPA70, etc., European Standards IEC/EN 61058-1, IEC/EN 61347-2-11, IEC/EN 61347-1, etc., Australian standards AS/NZS3123, AS/NZS3131, AS/NZS60320.1 AS/NZS60320.2.2, etc., Japanese standards JIS C 8281-2-1, etc., and Chinese standards GB16915.1, GB16915.2, GB16915.3, EN60669, etc. The voltage, frequency, and household power supply standards listed above are only provided for illustration purposes, and other types of voltage, frequency, and household power supply standards may also be applied to the physiological sign information acquisition system. For example, a power supply may also be wirelessly connected to the physiological sign information acquisition system, for example, energy may be transmitted from the power supply to the information acquisition system through inductive coupling. The technique may also transmit energy to the battery for operations of the information acquisition system.

The physiological sign information acquisition system may also use a battery (also be referred to as "a storage battery") as a power supply. The battery may include but not limited to a disposable battery, and also may be a rechargeable battery. The type of battery may include but not limited to a lead-acid battery, a nickel-cadmium battery, a nickel-metal hydride battery, a lithium ion battery, a fuel cell, a zinc-manganese battery, an alkaline manganese battery, a lithium battery, a mercury battery, and a zinc-mercury battery. The type of the battery may also be any other type. If a rechargeable battery is used, the battery may be charged by an interface of the physiological sign extraction system. The battery may be taken out to be charged or the battery may be charged using a wireless charging technology.

The external device 230 may generally refer to various direct or indirect devices related to a device of the physiological sign information acquisition system. The external device 230 may be local or remote, wired or wireless. For example, the external device 230 may include but not limited to an external display, an alarm, a pager, a cell phone, a computer, a tablet, a telephone, a video recorder, etc.

The processing module 202 may be connected to the receiving module 201 and the I/O module 203 respectively and the connection mode may be wired or wireless. The receiving module 201 may be connected with the I/O module 203 and the connection mode may be wired or wireless. The receiving module 201, the processing module 202, and I/O module 203 may include an individual power supply respectively, or two, three, or more of the modules may share a same power supply. The receiving module 201, the processing module 202, and the I/O module 203 may be connected to the external device respectively, a single external device may be connected with one or more modules, and the connection mode may be wired or wireless. The processing module 202 may be connected to one or more other processing modules (not shown), a storage device (not shown), and/or a cloud server (not shown), and the connection mode may be wired or wireless. The modules and devices described above are not essential. For persons having ordinary skills in the art, after understanding the contents and principles of the present disclosure, may make various variations and modifications in the form and details of the system without departing from the principles of the present disclosure. Modules may be combined with each other randomly or constitute a subsystem connected with other modules. However, those variations and modifications are within the scope of the claims of the present disclosure. For example, the receiving module 201 and the I/O module 203 shown in FIG. 2 may constitute a subsystem, and further the subsystem may be connected to the external device in a wired or wireless mode. Similar variations are within the scope of the claims of the present disclosure.

Figure 3:
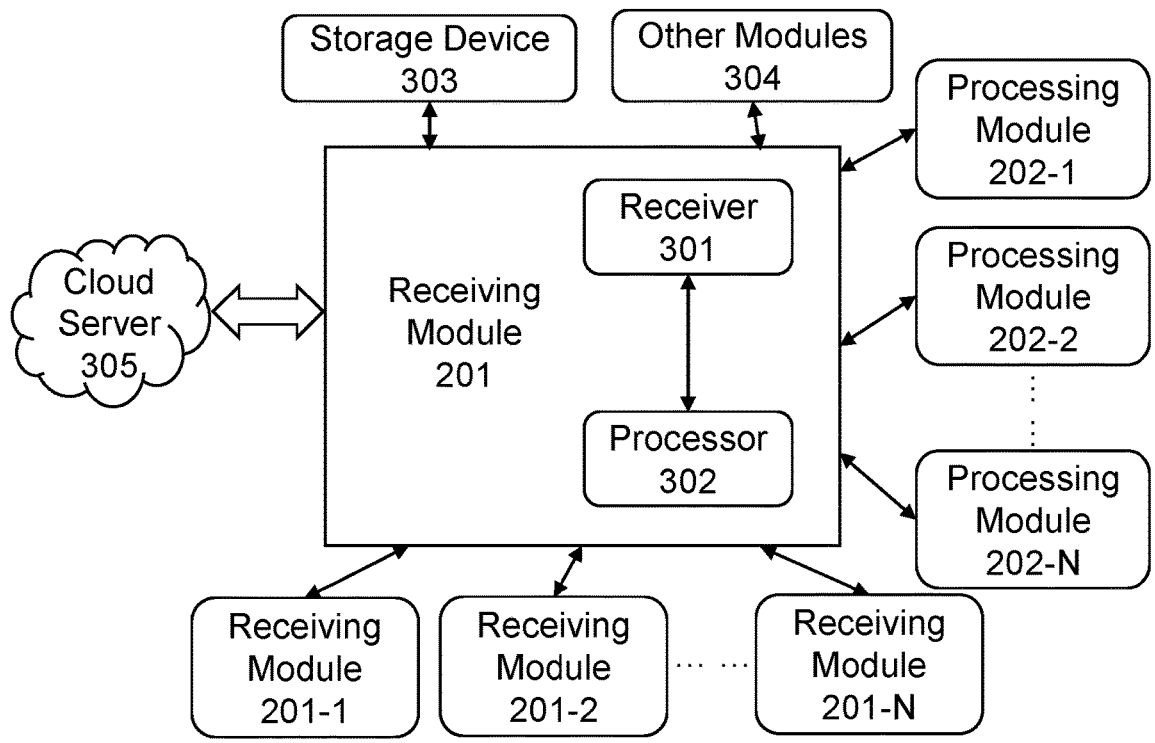
FIG. 3 is a schematic diagram illustrating a receiving module in the physiological sign information acquisition device and surrounding modules in the present disclosure.

FIG. 3 is a schematic diagram of the receiving module 201 and surrounding devices. The receiving module 201 may include but not limited to one or more receivers 301 and one or more processors 302. The receiving module 201 may be connected to a storage device 303 and other modules 304. The storage device 303 may also be included in the receiving module 201. In addition, the receiving module may be selectively connected to one or more other receiving modules 201-1, 201-2, . . . , and 201-N, or may not be connected to other receiving modules. The receiving module 201 may also be selectively connected to one or more other processing modules 202-1, 202-2, . . . , and 202-N, or may not be connected to other processing modules. The receiving module 201 may also be connected to the cloud server 305. All the connections mentioned may be wired or wireless. The connection relationship in the receiving module 201 and the connection relationship between the receiving module 201 and the surrounding devices are not limited to those shown in FIG. 3.

The receiving module 201 may receive the physiological information according to a preset condition. The physiological information may be affected by current blood vessels, vascular elasticity, a physiological condition of the living body, etc. For example, heart rates, respiratory rates, and blood pressures may be different before and after sports, the situations may be different before and after taking medicine, and the physiological signs may be different before and after sleeping. Therefore, when calculating an actual physiological sign, external factors and internal factors of the living body should be taken into account, and sign parameters should be preset and transmitted to the following processing module. For example, a corresponding motion compensation module may be integrated in the receiving module 201 to remove the interference caused by movement/vibration of the living body. The motion compensation module may be implemented by a hardware filter, a software filter, a photoelectric sensor, an acceleration sensor, a vibration sensor, or the like, or any combination thereof. In addition, the motion compensation module may remove the motion/vibration noise in the pulse wave by adjusting the sensor. In addition, the receiving module may include electronic or mechanical devices including not limited to a temperature sensor, a photoelectric detector, a pressure sensor, and a light emitting diode. The sensor may be affected by factors including but not limited to light intensity, skin tone, skin roughness, skin temperature, skin humidity, ambient temperature, ambient humidity, etc., therefore, it may be necessary to integrate a corresponding environment adaptation module in the collection module, such as a correction module or a compensation module corresponding to the environmental factor. For persons having ordinary skills in the art, after understanding the contents and principles of the present disclosure, may make variations and modifications in the form and details of the system without departing from the principles of the present disclosure. However, those variations and modifications are within the scope of the claims of the present disclosure. For example, sign parameters may be set in the receiving module or may be set according to data in a database where the sign parameters may be pre-stored. However, those variations and modifications are within the scope of the claims of the present disclosure. In addition, the above-mentioned correction module or compensation module may also be integrated into the pre-processing module, the processing module, or the calculation module, and the above-mentioned modifications, variations, or changes of the physiological sign system are within the scope of the claims of the present disclosure.

All data that have been acquired and processed by the receiving module 201 may be selectively stored in the storage device 303 and the cloud server 305 for subsequent processing. The storage device 303 mentioned herein may generally refer to all media that may read and/or write information, for example but not limited to, a random access memory (RAM) and a read only memory (ROM). The RAM may include but not limited to a decimal counting tube, a selectable tube, a delay line memory, a Williams tube, a dynamic random access memory (DRAM), a static random access memory (SRAM), a thyristor random access memory (T-RAM), a zero capacitor random access memory (Z-RAM), etc. The ROM may include not limited to a magnetic bubble memory, a magnetic twister memory, a thin-film memory, a magnetic plated wire memory, a magnetic core memory, a magnetic drum memory, an optical disk drive, a hard disk, a tape, an early NVRAM (nonvolatile memory), a phase change memory, a magnetoresistive random access memory, a ferroelectric random access memory, a nonvolatile SRAM, a flash memory, an electrically-erasable rewritable read only memory, an erasable programmable read only memory, a programmable read-only memory, a shielded heap memory, a floating-connected gate random access memory, a nano-random access memory, a track memory, a resistive random-access memory, a programmable metallization unit, etc. The above-mentioned storage devices are merely for illustration purposes, not intended to limit the storage devices that the system can use.

Additionally, data may be read and written by a cloud storage. The cloud storage may be a part of a cloud computing which implement a centralized storage and processing of data by connecting one or more groups of remote servers via a network. The cloud server 305 used in the physiological sign extraction system may be public, personal, or both. For example, the extracted physiological information, the data used by the processing module and the corresponding parameters may be stored and calculated in the personal cloud. The personal cloud herein may require an identification in the process of reading and writing, and data of general formula or methods of some vital signs may be obtained from the public cloud. The processing module 202 may select and read data in the personal cloud and the public cloud.

Figure 4:
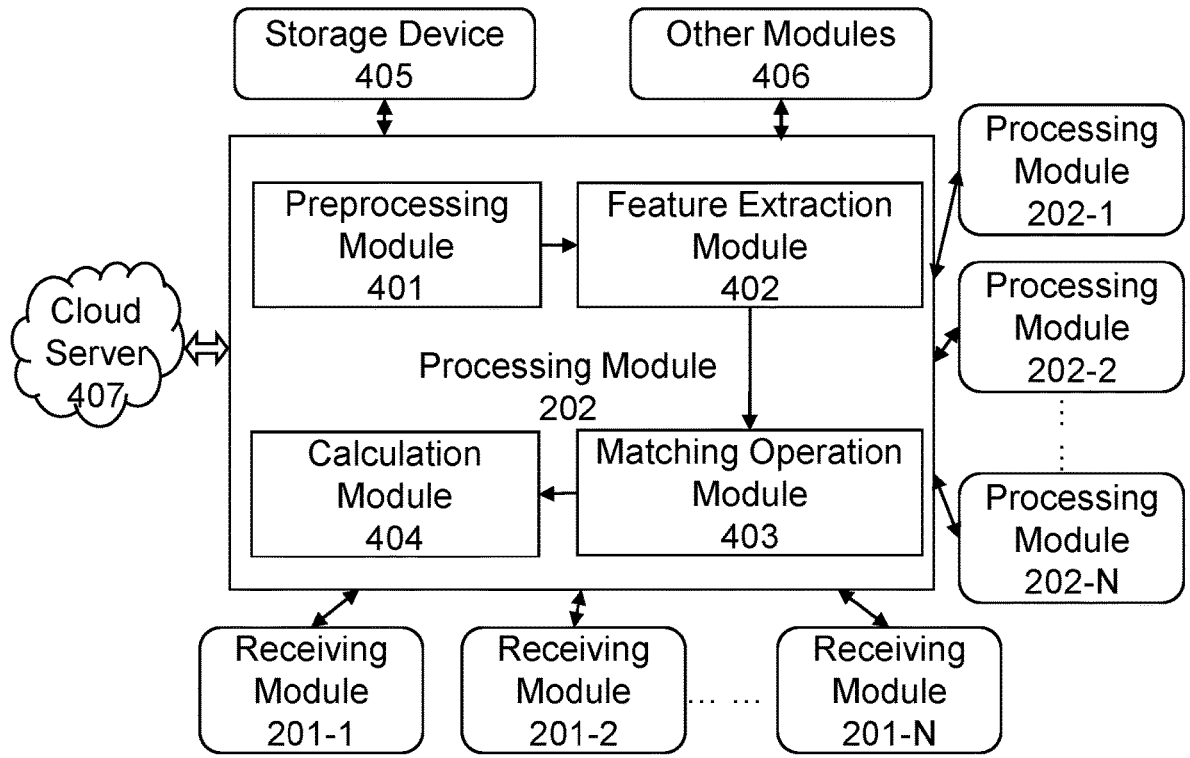
FIG. 4 is a schematic diagram illustrating a processing module in the physiological sign information acquisition device and surrounding modules in the present disclosure.

FIG. 4 is a schematic diagram of a connection between the processing module 202 and surrounding devices. The processing module 202 may include but not limited to one or more preprocessing modules 401, one or more feature extraction modules 402, one or more matching operation modules 403, and one or more calculation modules 404. The preprocessing module 401 may preprocess the physiological sign information and transmit the preprocessed physiological information to the feature extraction module 402. The feature extraction module 402 may extract a first feature and a second feature of the preprocessed physiological information and transmit the first feature and the second feature to the matching operation module 403. The matching operation module 403 may perform a matching operation on the first feature and the second feature, mark matching results, generate a third feature according to the results of the matching operation, and transmit the third feature and the preprocessed physiological information to the calculation module 404. The calculation module 404 may calculate the physiological sign of the human body according to the third feature of the preprocessed physiological information and/or the preprocessed physiological information. The processing module 202 may be connected to a storage device 405 and other modules 406. The storage device 405 may also be included in the processing module 202. In addition, the processing module 202 may be selectively connected to one or more other receiving modules 201-1, 201-2, . . . , 201-N, or may not be connected to other receiving modules. The processing module 202 may also be selectively connected to one or more other processing modules 202-1, 202-2, . . . , 202-N, or may not be connected to processing modules. The processing module 202 may also be connected to a cloud server 407. All the mentioned connections may be wired or wireless. The connections in the processing module 202 and the connections between the processing module 202 and the surrounding devices are not limited to those shown in FIG. 4. The processing module 202 may also receive the physiological information directly from one or more modules of the storage device 405, the other modules 406, the cloud server 407, the receiving module 201, and other processing modules, and may store the processed physiological sign information in one or more modules of the storage device 405, the other modules 406, the cloud server 407, the receiving module 201, and other processing modules. Similar variations and modifications are within the scope of the claims of the present disclosure.

The preprocessing module 401 may preprocess the received physiological information. The preprocessing process may include but not limited to a filtering process. The preprocessing module 401 may include two or more sub-preprocessing modules. The preprocessing process may include preprocessing the physiological information in serial or cascade or controlling one or more sub-preprocessing module by the control module (not shown) to preprocess the physiological information. The plurality of sub-preprocessing modules may or may not be associated with each other. The sub-preprocessing module may include one or more preprocess processes. The plurality of preprocessing processes may be preprocessing the physiological information in serial or in parallel. The preprocessing processes may include but not limited to low pass filtering, bandpass filtering, passband filtering, wavelet transform filtering, morphological filtering, Hilbert-Huang transformation, or the like, or any combination thereof. The preprocessing process may be in forms of a time domain, a frequency domain, and/or a combination thereof. The preprocessing module described above is not essential, and for persons having ordinary skills in the art, after understanding the contents and principles of the present disclosure, may make variations and modifications in the form and details of the system without departing from the principles of the present disclosure. However, those variations and modifications are within the scope of the claims of the present disclosure. For example, in the preprocessing process, a local transformation between time domain and frequency domain may be performed by using a technique including but not limited to a wavelet analysis and a multi-scale refinement analysis may be performed on the signals to extract useful information from the physiological information. It should be also noted that the preprocessing module 401 is not essential for the processing module 202, and the preprocessing module may be eliminated or not participate in the process of acquiring the physiological sign. Similar variations are within the scope of the claims of the present disclosure.

The feature extraction module 402 may receive information including but not limited to the physiological information preprocessed by the preprocessing module 301. The feature extraction module 402 may also directly or indirectly receive the unprocessed physiological information. The feature extraction module 402 may extract the first feature and the second feature of the preprocessed physiological information. The first feature and the second feature may be the same or not. The first feature and the second feature may include one or more feature values of features such as an amplitude, a frequency, a peak, a valley, a noise result, time information, a period, and an envelope of the preprocessed physiological information. The feature extraction module 402 may extract the first feature of the physiological information by using the first technique and extract the second feature of the physiological information by using the second technique. The first technique and the second technique may be the same or not. The first technique and the second technique may include a threshold method, a syntactic pattern recognition, a Gaussian function decomposition method, a wavelet transformation, a HTT method, a QRS wave detection algorithm, a local peak detection algorithm, a peak detection algorithm, a linear discriminant analysis, a quadratic discriminant analysis, a maximum entropy classifier, a decision tree, a decision table, a kernel estimation, a neighbor method, a naive Bayesian classifier, a neural network, a visual sensor, a support vector machine, gene expression programming, hierarchical clustering, k-means clustering, correlation clustering, a kernel principal component analyze, a lifting method, a Bayesian network, a Markov random field, a multiple linear principal component analysis, a Kalman filter, a particle filter, Gaussian process regression, linear regression or expansion, an independent component analysis, a principal component analysis, a conditional random field, a hidden Markov model, a maximum entropy Markov model, a recurrent neural network, an associative rule, inductive logic programming, similarity measure learning, a depth neural network, a depth belief network, a convolution neural network, a convolution depth belief network, etc. The particular technique may be any of the above techniques or any combination thereof. The various techniques may be related with each other directly or indirectly. The feature extraction described above may be unnecessary, and for persons having ordinary skills in the art, after understanding the contents and principles of the present disclosure, may make variations and modifications in the form and details of the system without departing from the principles of the present disclosure. However, those variations and modifications are within the scope of the claims of the present disclosure. For example, the first technique described above may consist of the threshold method and the wavelet transform in series or parallel. The feature extraction technique may be replaced by other techniques which may extract the amplitude, the frequency, the peak, the valley, the noise result, the time information, the period, and the envelope of the physiological information, and similar variations are within the scope of the claims of the present disclosure. As another example, the feature extraction 402 may be divided into two feature extraction modules (not shown). The two feature extraction modules may use the same or different techniques to extract the same feature value or different feature values of the physiological information, and similar inventions and variations are within the scope of the claims of the present disclosure. As a further example, the techniques listed above may be used to extract the first feature, the second feature, . . . , and an Nth feature of the physiological information, wherein N is an integer not less than 2. The matching operation module 403 may perform a matching operation on the first feature, the second feature, . . . , and the Nth feature, mark the matching results, generate a N+1th feature according to the matching results, and transmit the N+1th feature and the preprocessed physiological information to the calculation module 404.

The matching operation module 403 may receive information including the physiological information, the preprocessed physiological information, the first feature, the second feature, or the like, or a combinaiton thereof. The matching operation module 403 may perform a matching operation on the received information. The matching operation may include but not limited to a range matching, a value matching, a time point matching, an envelope matching, or the like, or any combination thereof. Then the matching operation module 403 may mark matching results. The marking may include but not limited to marking matched results, marking unmatched results, marking matched results and unmatched results respectively, etc. A third feature value of the physiological information may be generated based on the marked results. The third feature value may include but not limited to an amplitude, a frequency, a peak, a valley, a noise result, time information, a period, and an envelope of the preprocessed physiological information. The above-mentioned matching operation may be unnecessary, and for persons having ordinary skills in the art, after understanding the contents and principles of the present disclosure, may make variations and modifications in the form and details of the system without departing from the principles of the present disclosure. However, those modifications and variations are within the scope of the claims of the present disclosure. For example, the matching operation module 403 may perform a next operation based on the matching results instead of generating the third feature value, and similar variations are within the scope of the claims of the present disclosure.

The calculation module 404 may receive the physiological information, the preprocessed physiological information, a first feature value of the physiological information, a second feature value of the physiological information, a third feature value of the physiological information, marked matching results, or the like, or combination thereof. The calculation module may calculate a physiological sign based on the received information. A method used for calculating the physiological sign may include but not limited to a direct calculation, an intermittent calculation, a continuous calculation, a compensation calculation, a wave velocity measurement, a characteristic parameter measurement, a tension measurement, or the like, or any combination thereof. The methods may be related with each other or not. The methods may be related with each other directly or indirectly. The methods may be related with each in parallel or series. A method based on a feature value or the matching results may include but not limited to eliminating a point marked based on the feature value and the matching results, weakening an impact of the point marked based on the feature value and the matching results, strengthening the impact of the point marked based on the feature value and the matching results, ignoring the impact of the point marked based on the feature value and the matching results, or the like, or any combination thereof. The physiological sign may include but not limited to a blood pressure, a PR value, a blood oxygen saturation, a heart rate, a heart murmur, a bowel sound, a PH value, a creatinine content, a transferase content, a body temperature, a carcinoembryonic antigen content, or the like, or any combination thereof. The above-mentioned methods of the calculation module may be unnecessary, and for persons having ordinary skills in the art, after understanding the contents and principles of the present disclosure, may make modifications and variations in the form and details of the system without departing from the principles and configuration of the present disclosure. However, those modifications and variations are within the scope of the claims of the present disclosure. For example, the calculation module may determine multiple physiological signs by one method when calculating the physiological sign, or determine one physiological sign by multiple methods. The modification and variation associated with generating one or more types of physiological signs in the calculation module is within the scope of the claims of the present disclosure.

It should be noted that a physiological sign of a living body may vary with different conditions. For example, a "white coat" phenomenon may result in a temporary increase of the blood pressure. The physiological sign of the living body may also differ when the living body is located at home, company, shopping mall, park, gym, leisure place, or other places. The physiological sign, such as the blood pressure, may also differ greatly when the living body is in different moods such as happiness, anger, nervousness, depression, fear, sadness, or anxiety. In this situation, a single measurement of the physiological sign may not reflect true conditions of physiological sign. Therefore, it may be necessary to perform measurements at different time periods such as morning, noon, nightfall, and evening when calculating the physiological sign. It may also be necessary to perform measurements based on different events such as before or after taking medicine, before or after meals, and before or after exercising. It may also be necessary to perform one or more measurements on the living body, including but not limited to processing the physiological signs obtained by multiple measurements according to a certain rule. For example, an average physiological sign may be determined based on physiological signs, or the physiological sign of the living body may be obtained by a calibration according to parameter estimation and optimization based on a database, such as a curve fitting, an artificial neural network, etc. For persons having ordinary skills in the art, after understanding the contents and principles of the present disclosure, may make modifications and variations in the form and details of the system without departing from the principles and configuration of the present disclosure. However, those modifications and variations are within the scope of the claims of the present disclosure. For example, one or more groups of physiological sign values may be added to the processing module or the calculation module for comparison to generate a relatively true physiological sign value. The modification and variation are within the scope of the claims of the present disclosure.

Figure 5:
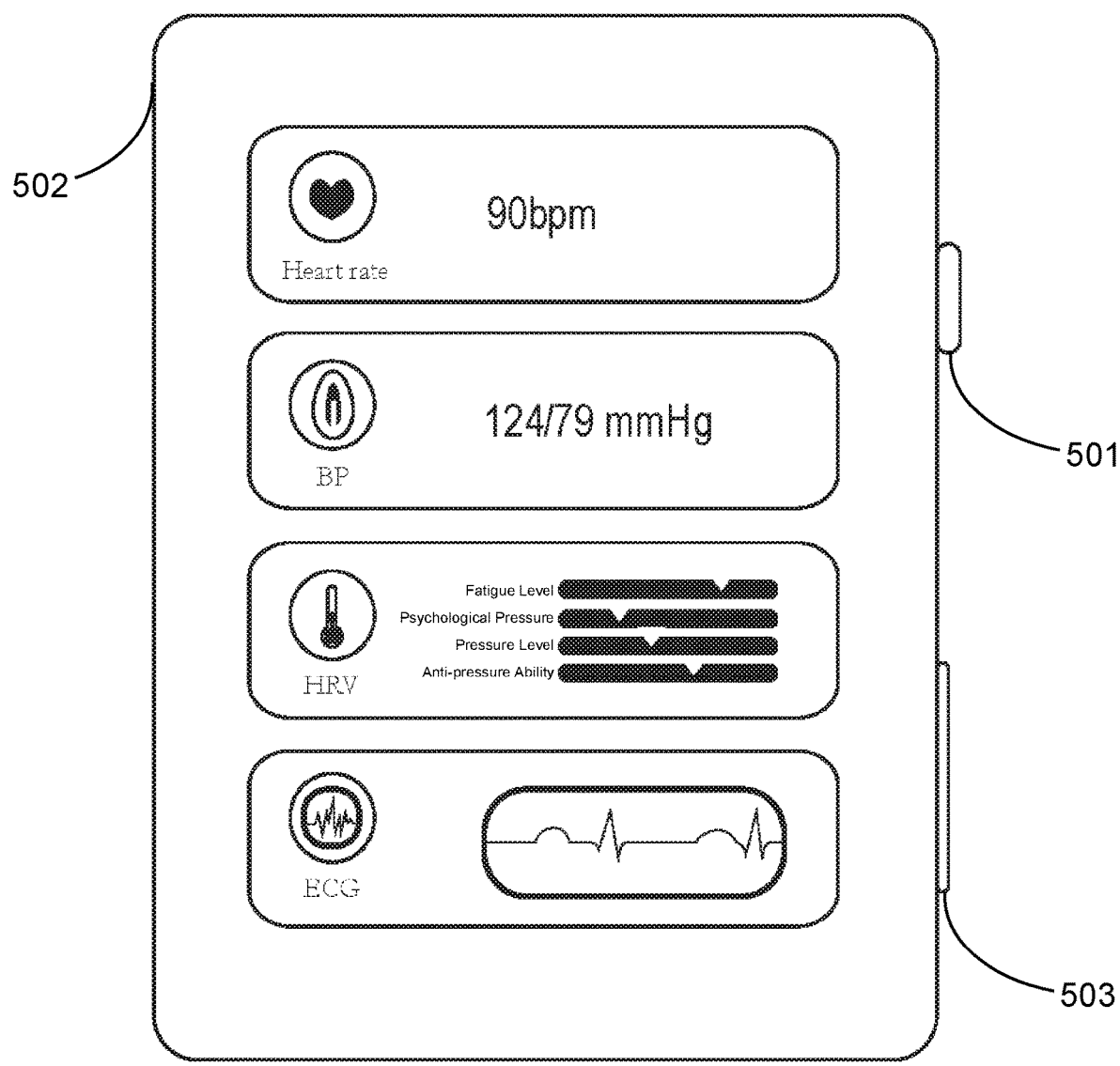
FIG. 5 is a schematic diagram illustrating an I/O module in the physiological sign information acquisition device in the present disclosure.

FIG. 5 is a schematic diagram of the I/O module 203. The I/O module 203 may include but not limited to an input key 501 and a screen 502. The input key 501 may be used as a function key, a functional short-cut key, a return short-cut key, or a menu short-cut key. The input key 503 may be a mechanical key, an electronic trigger key, or a touch button. The screen 502 may have an input function, an output function, or both. The screen 502 may be an operation interface for a user to use the physiological sign information extraction system. A type of input/output information may include but not limited to numbers, analogs, texts, voices, graphic images, etc. A type of the screen 502 may include but not limited to an electronic screen, a plasma screen, a resistance technology touch screen, a capacitive touch screen, an infrared technology touch screen, a surface acoustic wave technology touch screen, etc., The screen 502 may also be selected according to specific using requirements The I/O module 203 may determine to input/output one or more physiological signs including but not limited to a blood pressure, a PR value, a blood oxygen saturation, a heart rate, a heart murmur, a bowel sound, a PH value, a creatinine content, a transferase content, a body temperature, a carcinoembryonic antigen content, etc. The contents displayed on the screen may or may not be set by the input key 501. The contents displayed on the screen may or may not be set by the system default. The I/O module 203 may input/output one or more types of information including local real-time weather information, weather forecast, room temperature, air humidity, time in all time zones around the world, etc. The I/O module 203 may provide an explanation or further dig associated with the physiological sign information, for example, whether there are abnormal physiological signs, body conditions of the user indicated by the physiological sign, including but not limited to a health index, a compression index, a blood oxygen concentration, blood lipid concentration, whether the physiological sign indicating a health concern of the user, etc. The I/O module 203 may transmit contents needed to be output to the screen for displaying, transmit contents needed to be output to other devices, or transmit contents needed to be output to a storage device or a cloud server. It should be noted that the I/O module 203 may be integrated on the physiological sign information acquisition device, and may also be modified on a basis of implementing an input/output function. For example, the I/O module 203 may be integrated as an input or output device on an external device such as a watch, a bracelet, a neck ring, a sphygmomanometer, a breath detector, a cell phone, a laptop, a tablet computer, etc. However, those modifications and variations are within the scope of the claims of the present disclosure.

The modules in the physiological sign extraction system, the external devices, the storage device, and the cloud server may be connected to each other via a wired connection or a wireless connection. The wired connection may include but not limited to a metal cable, an optical cable, or a hybrid cable, such as a coaxial cable, a communication cable, a flexible cable, a spiral cable, a non-metallic sheathed cable, a metallic sheathed cable, a multi-core cable, a twisted pair cable, a ribbon cable, a shielded cable, a telecommunication cable, a double cable, a parallel double core wire, and a twisted pair. The above-mentioned examples are merely provided for illustration purposes, and a medium of the wired connection may be a medium with other types such as a transmission carrier of electrical signals or optical signals. The wireless connection may include but not limited to a radio communication, a free space optical communication, an acoustic communication, an electromagnetic induction, etc. The radio communication may include but not limited to IEEE802.11 standard, IEEE802.15 standard (e.g., Bluetooth technology and ZigBee technology, etc.), the first generation of mobile communication technology, the second generation of mobile communication technology (e.g., FDMA, TDMA, SDMA, CDMA, SSMA, etc.), the third generation of mobile communication technology (e.g., CDMA2000, WCDMA, TD-SCDMA, WiMAX, etc.), the fourth generation of mobile communication technology (e.g., TD-LTE and FDD-LTE, etc.), satellite communication (e.g., GPS technology, etc.), and other technologies running in the ISM band (e.g., 2.4 GHz, etc.). The free space optical communication may include but not limited to visible light signals, infrared signals, far infrared signals, etc. The acoustic communication may include but not limited to sound wave signals, ultrasonic signals, etc. The electromagnetic induction may include but not limited to near field communication technology, etc. The above-mentioned examples are merely provided for illustration purposes, and a medium of the wireless connection may be a medium with other types such as Z-wave technology, other charged civilian radio bands and military radio bands, etc.

The connections between the modules of the physiological sign extraction system, the connections between the modules and external devices, and the connections between the system and a storage device or a cloud server are not limited to the above-mentioned technologies. The above connections may be used separately in the physiological sign information acquisition device or may be used in any combination of multiple connections. When the connections are used in any combination of multiple connections, corresponding gateway devices may be required for information interaction. The modules may be integrated together so as to implement functions of at least one module by one device. The modules may be distributed on different electronic elements, more than one module may be integrated on a same electronic element, or a module may be distributed on more than one electronic element. An external device may be integrated in an implementing device of one or more modules, and one or more modules may also be integrated in one or more external devices.

Figure 6:
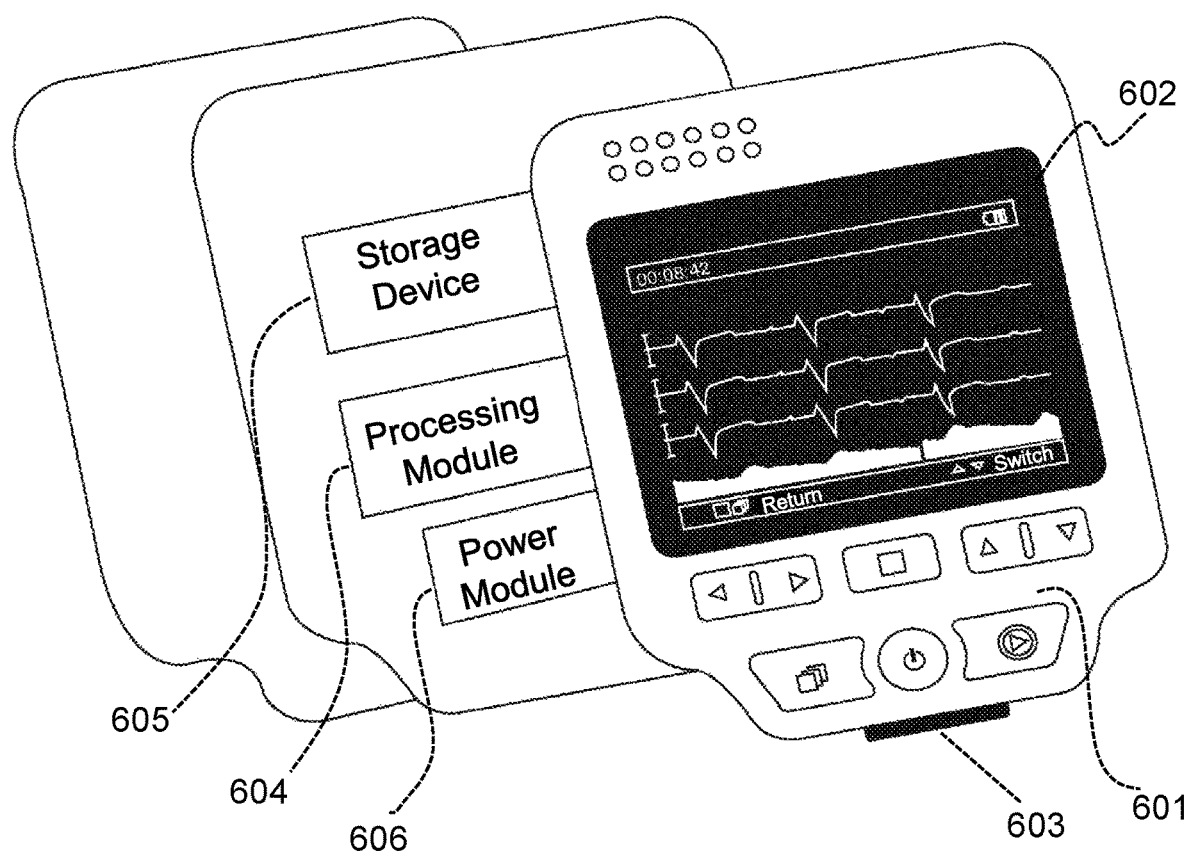
FIG. 6 is a schematic diagram illustrating a physiological sign information acquisition device in the present disclosure.
Figure 11:
FIG. 11 is a schematic diagram illustrating a time relationship between ECG signals and PPG signals in the present disclosure.

FIG. 6 is a specific embodiment of the physiological sign extraction system. As shown in FIG. 6, the system may include but not limited to a function key 601, one or more display screens 602, one or more measuring terminals 603, one or more processing modules 604, one or more storage devices 605, and one or more power modules 606, etc. The function key 601 may include a power key. The function key 601 may further include one or more keys for different functions including but not limited to up-and-down adjustment, waveform display, stop, pause, return, multi-screen display, navigation, quick measurement, etc. It should be noted that implementing of the function key may include but not limited to a mechanical key or an inductive touch button. Further, multiple forms (e.g., a light-sensitive key or an electronic key) that can implement the function key may be within the scope of the claims of the present disclosure. The display screen 602 may be a LCD screen, an electronic screen, a plasma screen, a resistance technology touch screen, a capacitive touch screen, an infrared technology touch screen, a surface acoustic wave technology touch screen, etc. The display screen 602 may also implement the function of the function key 601. The function key 601 may be displayed on the display screen 602 and implemented by the display screen 602. The display screen 602 may display one or more physiological signs (e.g., an ECG waveform, a blood pressure, a PR value, a blood oxygen saturation, a heart rate, a heart murmur, a bowel sound, a PH value, a creatinine content, a transferase content, a body temperature, a carcinoembryonic antigen content, etc.) on a same screen (see FIG. 11). The measuring terminals 603 may measure a physiological sign of the living body based on one or more measurements such as a lead measurement, a chest measurement, a leg measurement, a hand measurement, etc. The processing module 604 may further process the physiological information measured by the measuring terminal to generate the physiological sign including but not limited to one of more of an ECG waveform, a blood pressure, a PR value, a blood oxygen saturation, a heart rate, a heart murmur, a bowel sound, a PH value, a creatinine content, a transferase content, a body temperature, a carcinoembryonic antigen content, etc. The storage module 605 may be used to store physiological sign data in a certain period or physiological sign data with a certain size. The storage device may refer to any medium for reading and/or writing information. The power module 606 may be used to provide electric power. The power module 606 may be a built-in power, a direct current, or an alternating current. The built-in power may be in various forms, such as a battery, a storage battery, a lithium battery, a rechargeable battery, etc. The modules in the above-mentioned specific embodiment may be unnecessary, and for persons having ordinary skills in the art, after understanding the contents and principles of the present disclosure, may make modifications and variations in the form and details of the system without departing from the principles and configuration of the present disclosure. However, and such modifications and variations are within the scope of the claims of the present disclosure. For example, the storage device 605 is limited to a local storage medium, and related data may be stored in a position that supports wireless storage such as a cloud server, an internet disk, etc. Similar modifications and variations are within the scope of the claims of the present disclosure. The storage range is not limited and may be adjusted according to an actual situation. A storage time range may be not less than one second and an upper limit may be determined according to a storage size, or the storage device may store data not less than 1 KB and an upper limit may also be determined according to the size of storage. The Modifications and variations associated with the range are also within the scope of the claims of the present disclosure.

Figure 7:
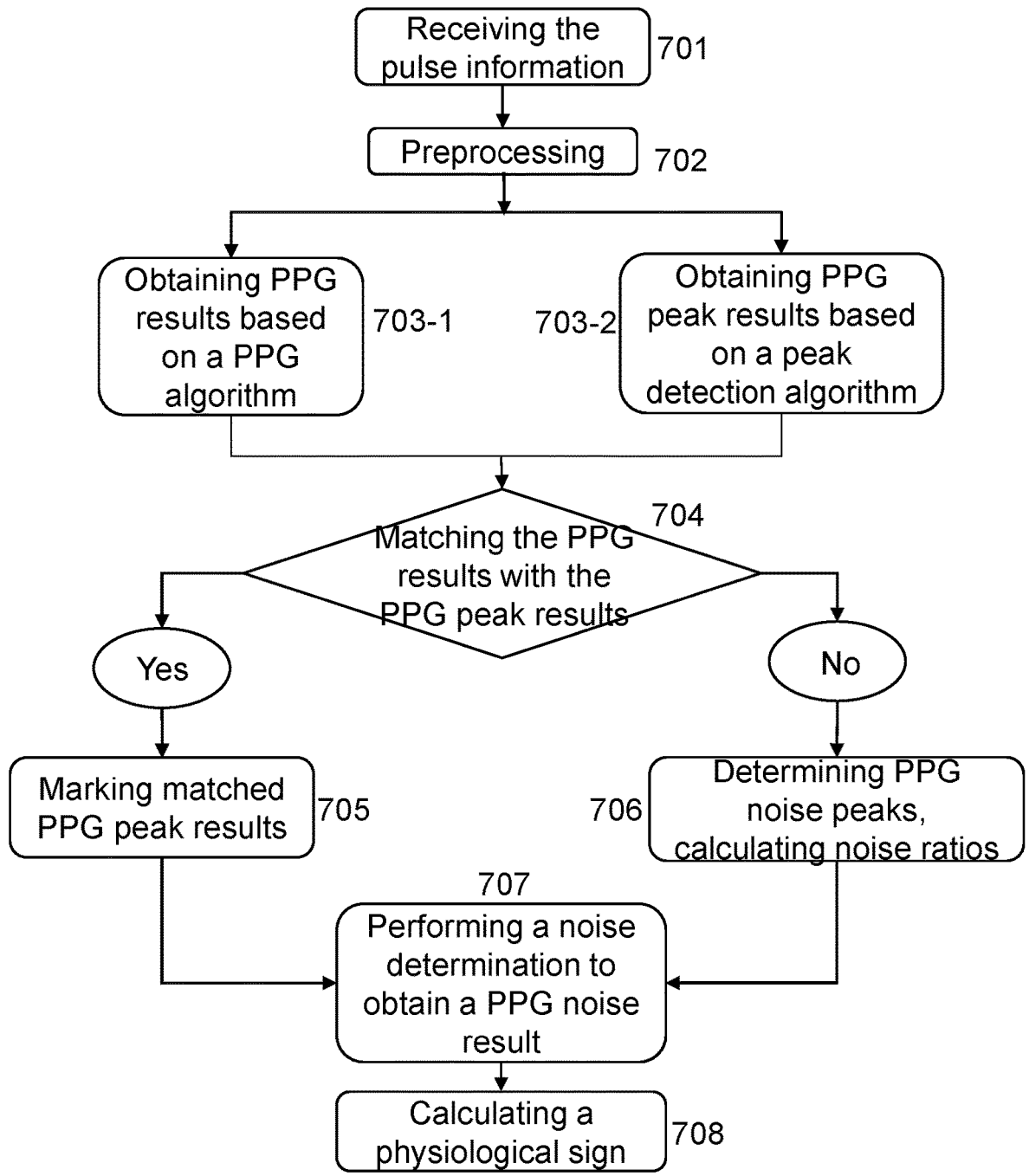
FIG. 7 is a flowchart illustrating a process for obtaining physiological sign information in the present disclosure.

FIG. 7 is a flowchart illustrating an exemplary process of an algorithm for detecting and processing noises in physiological sign information according to an embodiment. In this embodiment, input physiological sign information may be pulse information of a living body, wherein the pulse information may include noises. Firstly, the pulse information of the living body may be acquired.

As shown in FIG. 7, the processing steps of the algorithm may be illustrated as follows:

Step 701: the pulse information may be received;

Step 702: the pulse information may be preprocessed;

Step 703: PPG results and PPG peak results may be obtained from the preprocessed pulse information based on a PPG algorithm (step 703-1) and a peak detection algorithm (step 703-2);

Step 704: the PPG results may be matched with the PPG peak results;

Step 705: the matched PPG peak results may be marked in response to that the PPG results match with the PPG peak results;

Step 706: PPG noise peaks may be determined in response to that the PPG results do not match with the PPG peak results, noise peak amplitudes and a number of the PPG noise peaks may be recorded, and noise ratios may be determined based on the noise peak amplitudes;

Step 707: a noise determination may be performed to obtain a PPG noise result based on the noise ratios and the number of the PPG noise peaks;

Step 708: a physiological sign of the living body may be calculated based on the PPG noise result and the pulse information.

The steps may be described in details below:

The pulse information may be preprocessed in step 702. The preprocessing may include a filtering step. The filter may include a bandpass filter of 1 to 30 Hz, a low pass filter, a passband filter, a wavelet transform filter, a Hilbert-Huang transform filter, a morphological filter, or the like, or a combination thereof. The filter may filter the pulse wave signals. Multiple filters may be arranged in series or in parallel. It should be noted that the preprocessing step may be unnecessary.

The preprocessed pulse information may be processed to obtain the PPG results based on the PPG algorithm in step 703-1. The PPG algorithm may include but not limited to a threshold method, a syntactic pattern recognition, a Gaussian function decomposition method, a wavelet transformation, a HTT method, a QRS wave detection algorithm, a local peak detection algorithm, a peak detection algorithm, a linear discriminant analysis, a quadratic discriminant analysis, a maximum entropy classifier, a decision tree, a decision table, a kernel estimation, a neighbor method, a naive Bayesian classifier, a neural network, a visual sensor, a support vector machine, gene expression programming, hierarchical clustering, k-means clustering, correlation clustering, a kernel principal component analysis, a lifting method, a Bayesian network, a Markov random field, a multiple linear principal component analysis, a Kalman filter, a particle filter, Gaussian process regression, linear regression or expansion, an independent component analysis, a principal component analysis, a hidden Markov model, a maximum entropy Markov model, a recurrent neural network, an associative rule, inductive logic programming, similarity metrics learning, a deep neural network, a deep belief network, a convolutional neural network, a convolutional deep belief network, or the like, or any combination thereof. A peak detection may be performed on the pulse information to obtain the PPG peak results based on the peak detection algorithm in step 703-2. In some embodiments, the peak detection algorithm may include the following steps:

Firstly, data of the pulse information in a current window period (e.g., 4 s) may be obtained, and each data point may be determined according to the following steps:

Step a): 15 data points may be traced forward from on a current data point and a maximum value max1 within the range may be determined;

Step b): 15 data points may be traced backward from a current data point and a maximum value max2 within this range may be determined;

Step c): if the current data point is greater than both max1 and max2, the current data point may be determined as a peak; if not, the current data point may be ignored;

Step d): the peak determined in step 703c may be compared with a threshold. If the peak is greater than the threshold, the peak may be determined as a qualified peak and the peak may be marked; if not, the peak may be ignored.

During the process of the peak detection algorithm, a length of the window period may be set according to different situations and is not limited to 4 s, such as 1 s, 2 s, 3 s, . . . , Ns, wherein N may be any positive real number.

In steps a) and b), the number of data points traced forward or backward from the current data point is limited to 15, and may be 1, 2, 3, 4, 5, . . . , M, wherein M may be any positive integer.

In step d), an initial threshold may be obtained based on the peaks in an initial window period. For example, all the peak results in the initial window period may be averaged and multiplied by a certain coefficient (e.g., 0.4) to obtain the initial threshold. The threshold may be iteratively updated during the calculations in the following window periods. For example, qualified peaks in the current window period may be averaged and multiplied by the coefficient (e.g., 0.4), and averaged with a current threshold to obtain a new threshold.

In step 704, The PPG results and the PPG peak results determined in step 703-1 and step 703-2 may be matched (detailed description of the matching may be described in below). In step 705, the matched PPG peak results may be marked in step 705. In step 706, the unmatched PPG peak results may be determined as noise peaks. A noise ratio may be calculated according to a formula below:

Noise Ratio=Amplitude Value of Noise Peak/Average Amplitude Value of Matched Peaks where the Amplitude Value of Noise Peak may refer to an amplitude value of an unmatched PPG peak result and the Average Amplitude of Matched Peaks may refer to an average amplitude of the matched PPG peak results.

During the matching, if a difference between a characteristic parameter (e.g., a position of a peak) of a PPG result and that of a PPG peak result is within a certain range, it may indicate that the PPG result and the PPG peak result are matched, wherein the certain range may be, for example, 30 sample points.

In step 707, a noise determination may be performed. The steps of the noise determination may be described as follows:

Step a'): a noise result that the pulse information may include noise may be determined if the PPG results do not match to the PPG peak results or there is no PPG result in a window period;

Step b'): a noise result that the pulse information may include noise may be determined if the number of noise ratios not less than 1 is greater than a half of the number of the PPG result waves;

Step c'): a noise result that the pulse information may include noise may be determined if the number of noise ratios not less than 0.75 is greater than 0.75 times of the number of the PPG result waves;

Step d'): a noise result that the pulse information may include noise may be determined if the number of noise ratios not less than 0.5 is greater than the number of the PPG result waves.

The sequence of the steps a')~d') may be modified and the steps a')~d') may be arranged randomly. The modifications and variations to the steps are within the scope of the claims of the present disclosure.

In step 708, the physiological sign of the human body may be determined based on the noise result determined in step 706. The physiological signs may be calculated based on one or more methods such as eliminating the noise result determined in step 707, strengthening the noise result determined in step 707, weakening the noise result determined in step 707, etc. The physiological sign may include a blood pressure, a PR value, a blood oxygen saturation, a heart rate, a heart murmur, a bowel sound, a PH value, a creatinine content, a transferase content, a body temperature, a carcinoembryonic antigen content, or the like, or a combination thereof.

Figure 8:
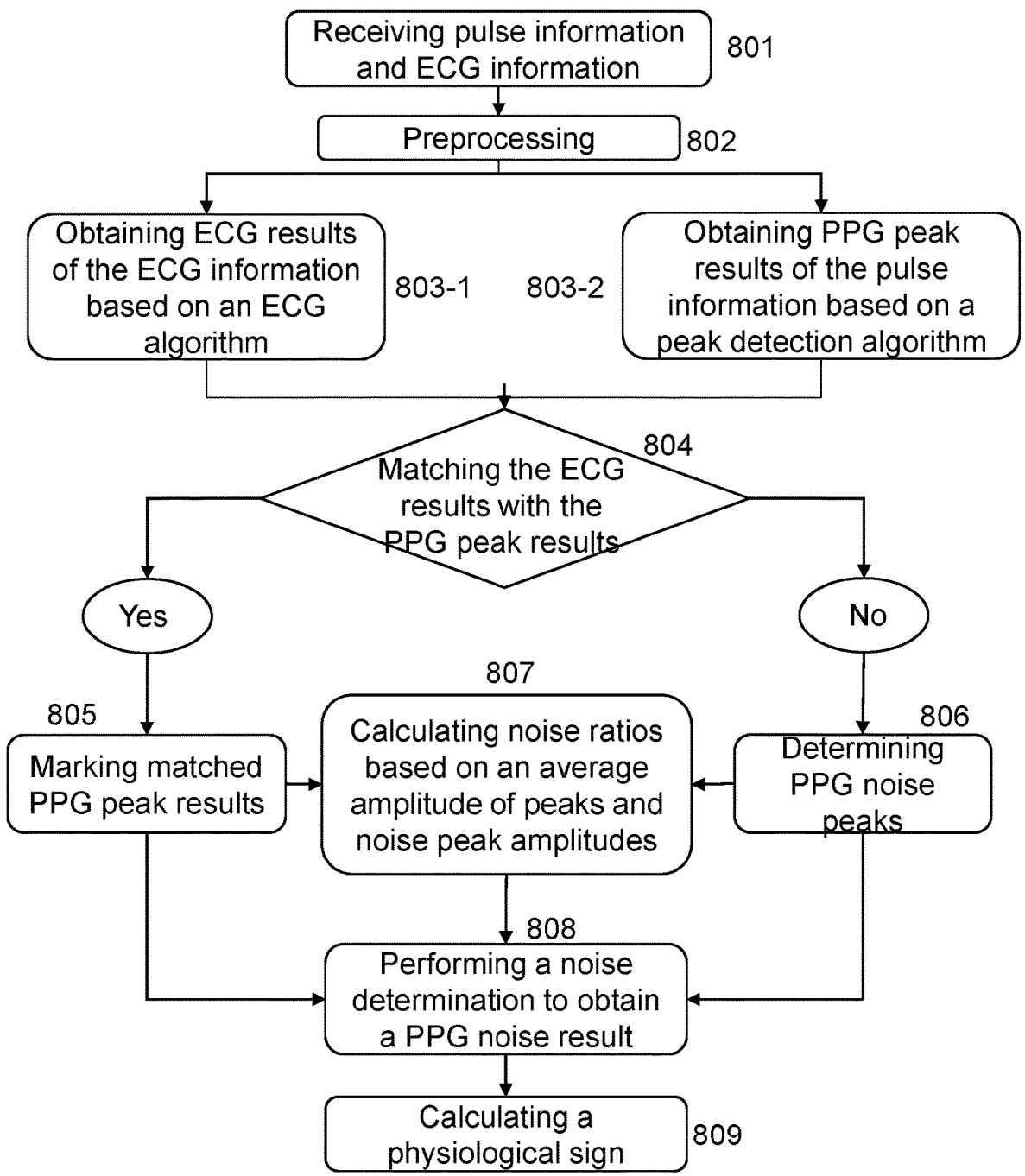
FIG. 8 is a flowchart illustrating a process for obtaining physiological sign information in the present disclosure.

FIG. 8 is another flowchart illustrating an exemplary process of an algorithm for detecting and processing noises in physiological sign information according to an embodiment. In this embodiment, the physiological sign information includes pulse information and ECG information. Firstly, the pulse information and the ECG information of the living body may be acquired.

As shown in FIG. 8, processing steps of the algorithm may be illustrated as follows:

Step 801: the pulse information and the ECG information may be received;

Step 802: the pulse information and the ECG information may be preprocessed via a filter;

Step 803: ECG results of the ECG information may be obtained based on an ECG algorithm (step 803-1) and PPG peak results of the pulse information based on a peak detection algorithm (step 803-2);

Step 804: the ECG results may be matched with the PPG peak results;

Step 805: the matched PPG peak results may be marked in response to that the ECG results match with the PPG peak results, and an average amplitude value of the pulse information may be calculated;

Step 806: PPG noise peaks may be determined in response to that the ECG results do not match with the PPG peak results, and noise peak amplitudes and the number of the PPG noise peaks may be recorded;

Step 807: noise ratios may be calculated based on the average amplitude value of the pulse information and the noise peak amplitudes;

Step 808: a noise determination may be performed to obtain a PPG noise result based on the noise ratios, the PPG noise peaks, and the matched PPG peak results;

Step 809: a physiological sign of the living body may be calculated based on the PPG noise result, the pulse information, and the ECG information.

The steps may be described in details below:

The pulse information and the ECG information may be preprocessed in step 802. The preprocessing may include a filtering step. The filter may include a bandpass filter of 1 to 30 Hz, a low pass filter, a passband filter, a wavelet transform filter, a Hilbert-Huang transform filter, a morphological filter, or the like, or a combination thereof. The filter may filter the pulse wave signals. Multiple filters may be arranged in series or in parallel. It should be noted that the preprocessing step may be unnecessary.

The preprocessed ECG information may be processed to obtain the ECG results based on the ECG algorithm in step 803. The ECG algorithm may include but not limited to a threshold method, a syntactic pattern recognition, a Gaussian function decomposition method, a wavelet transformation, a HTT method, a QRS wave detection algorithm, a local peak detection algorithm, a peak detection algorithm, or the like, or a combination thereof. It should be noted that the ECG algorithm may refer to any method based on which the ECG results can be obtained, and for persons having ordinary skills in the art, any alternative of the ECG algorithm may be within the scope of the claims of the present disclosure. A peak detection may be performed on the preprocessed ECG information to obtain the peak results based on the peak detection algorithm, wherein the steps of the peak detection algorithm may or may not be the same as that FIG. 7. Any detection algorithm based on which the peak results of the pulse information may be obtained is also within the scope of the claims of the present disclosure.

In step 804, the ECG results and the PPG peak results determined in step 803 may be matched (detailed description of the matching may be described in below). In step 805, the matched PPG peak results may be marked. In step 806, the unmatched PPG peak results may be determined as noise peaks. A noise ratio may be calculated according to a formula below:

Noise Ratio=Amplitude Value of Noise Peak/Average Amplitude Value of Matched Peaks where the Amplitude Value of Noise Peak may refer to an amplitude value of an unmatched PPG peak result and the Average Amplitude of Matched Peaks may refer to an average amplitude of the matched PPG peak results.

In the matching algorithm, a delay operation may be performed on the ECG results since an R wave may appear earlier than a PPG wave peak. For example, the number of delayed points may be 40, or any positive number with an absolute value not greater than 100. Then the matching may be performed according to the matching algorithm in FIG. 7.

In step 808, a noise determination may be performed. The steps of the noise determination may be described as follows:

Step 808a: a noise determination that the pulse information may not include noise may be determined if the ECG results report noise;

Step 808b: a noise determination that the pulse information may include noise may be determined if the ECG results are not matched with the PPG peak results;

Step 808c: a noise determination that the pulse information may include noise may be determined if the number of noise ratios not less than 1 is greater than half of the number of the ECG result waves;

Step 808d: a noise determination that the pulse information may not include noise may be determined if the number of noise ratios not less than 0.75 is greater than 0.75 times of the number of the ECG result waves;

Step 808e: a noise determination that the pulse information may not include noise may be determined if the number of noise ratios not less than 0.5 is greater than the number of the ECG result waves.

In step 809, the physiological sign of the living body may be calculated based on the noise result determined in step 808. The physiological sign may be calculated based on one or more methods such as eliminating the noise result determined in step 808, strengthening the noise result determined in step 808, weakening the noise result determined in step 808, etc. The physiological sign may include a blood pressure, a PR value, a blood oxygen saturation, a heart rate, a heart murmur, a bowel sound, a PH value, a creatinine content, a transferase content, a body temperature, a carcinoembryonic antigen content, or the like, or a combination thereof.

Figure 9:
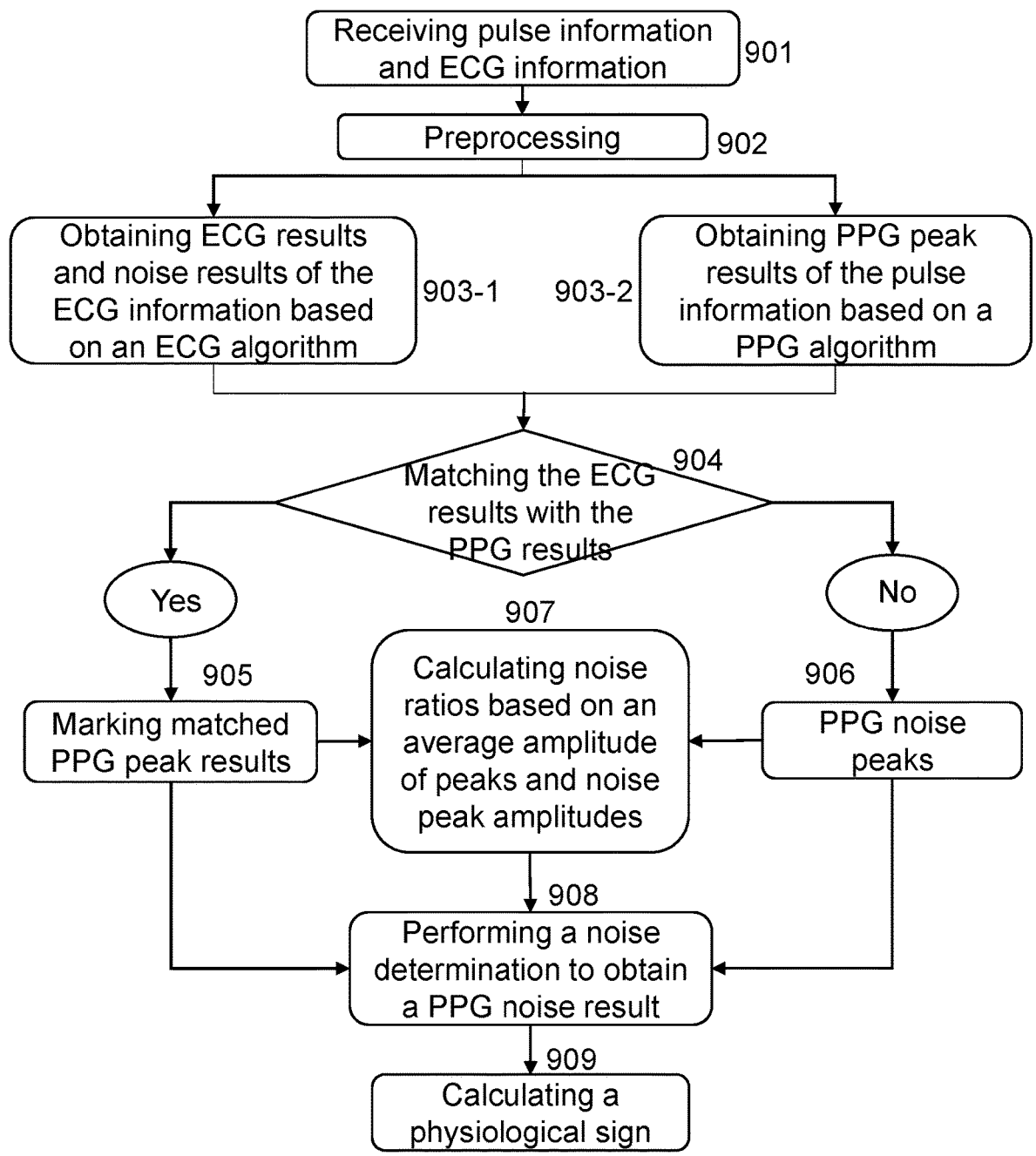
FIG. 9 is a flowchart illustrating a process for obtaining physiological sign information in the present disclosure.

FIG. 9 is another flowchart illustrating an exemplary process of an algorithm for detecting and processing noises in physiological sign information according to an embodiment. In this embodiment, the physiological information may include pulse information and ECG information of a living body. Firstly, the pulse information and the ECG information of the living body may be acquired.

As shown in FIG. 9, processing steps of the algorithm may be illustrated as follows:

Step 901: the pulse information and the ECG information may be received;

Step 902: the pulse information and the ECG information may be preprocessed;

Step 903: ECG results of the ECG information may be obtained based on an ECG algorithm and PPG peak results of the pulse information based on a peak detection algorithm, and ECG noise results may be recorded;

Step 904: the ECG results may be matched with the PPG peak results;

Step 905: the matched PPG peak results may be marked in response to that the ECG results match with the PPG peak results;

Step 906: PPG noise peaks may be determined in response to that the ECG results do not match with the PPG peak results;

Step 907: noise ratios may be calculated based on the PPG results after matching;

Step 908: a noise determination may be performed to obtain a PPG noise result based on the noise ratios and the PPG noise peaks;

Step 909: a physiological sign of the living body may be calculated based on the PPG noise result.

The steps may be described in details below:

The pulse information and the ECG information may be preprocessed in step 902. The preprocessing may include a filtering step. The filter may include a bandpass filter of 1 to 30 Hz, a low pass filter, a passband filter, a wavelet transform filter, a Hilbert-Huang transform filter, a morphological filter, or the like, or a combination thereof. The filter may filter the pulse wave signals. Multiple filters may be arranged in series or in parallel. It should be noted that the preprocessing step may be unnecessary.

The pulse information may be processed to obtain the PPG results based on the PPG algorithm in step 903. The ECG information may be processed to obtain the ECG results and the ECG noise results in a window period based on the ECG algorithm.

Step 904 may or may not be the same as step 804 in FIG. 8. Any matching algorithm based on which PPG matching peak results of the pulse information can be obtained may also be within the scope of the claims of the present disclosure.

The calculating of the noise ratios in step 907 may or may not be the same as that in 807.

In step 908, a noise determination may be performed. The steps of the noise determination may be described as follows:

Step 908*a*: a noise determination that the pulse information may not include noise may be determined if the ECG results report noise;

Step 908*b*: a noise determination that the pulse information may include noise may be determined if the ECG results are not matched with the PPG peak results;

Step 908*c*: a noise determination that the pulse information may include noise may be determined if the number of noise ratios not less than 1 is greater than half of the number of the ECG result waves;

Step 908*d*: a noise determination that the pulse information may include noise may be determined if the number of noise ratios not less than 0.75 is greater than 0.75 times of the number of the ECG result waves;

Step 908*e*: a noise determination that the pulse information may include noise may be determined if the number of noise ratios not less than 0.5 is greater than the number of the ECG result waves.

In step 909, the physiological sign of the living body may be calculated based on the noise result determined in step 908. The physiological sign may be calculated based on one or more methods such as eliminating the noise result determined in 908, strengthening the noise result determined in step 908, weakening the noise result determined in step 908, etc. The physiological sign may include a blood pressure, a PR value, a blood oxygen saturation, a heart rate, a heart murmur, a bowel sound, a PH value, a creatinine content, a transferase content, a body temperature, a carcinoembryonic antigen content, or the like, or a combination thereof.

Figure 10:
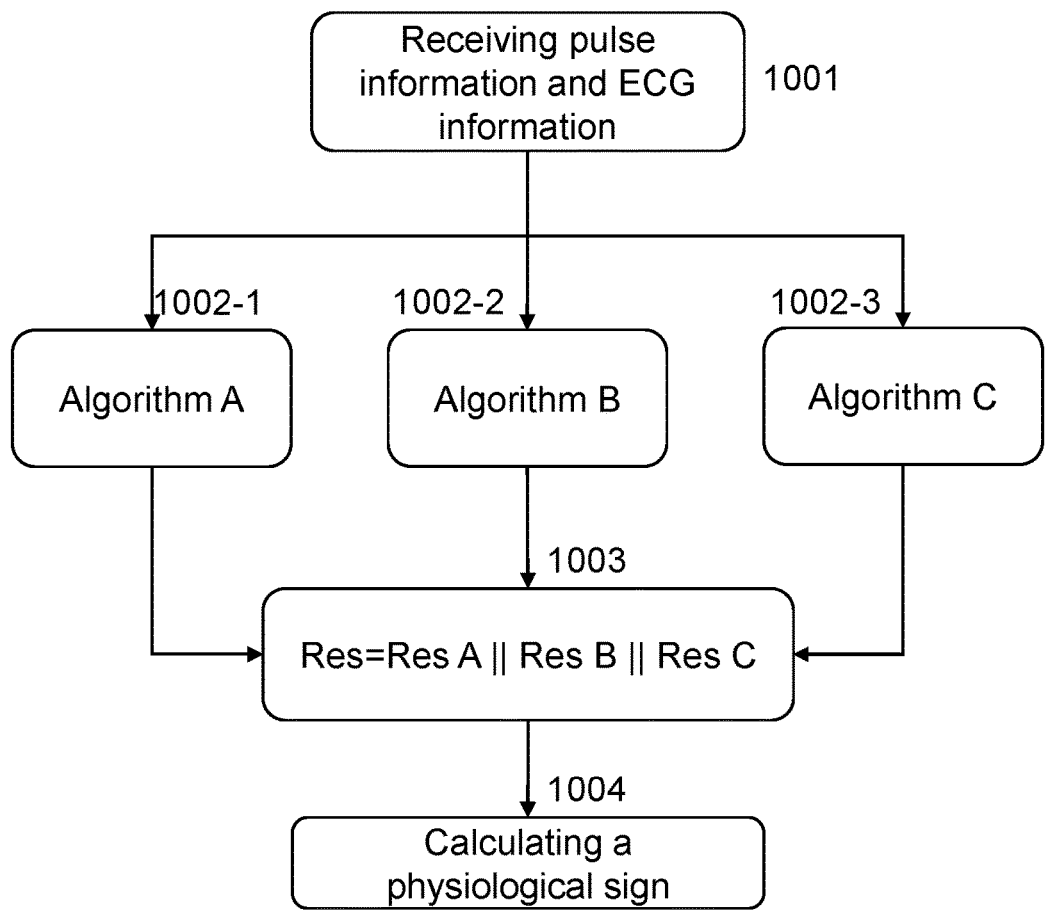
FIG. 10 is a flowchart illustrating a process for obtaining physiological sign information in the present disclosure.

FIG. 10 is another flowchart illustrating an exemplary process of an algorithm for detecting and processing noises in physiological sign information according to an embodiment. In this embodiment, the physiological information may include pulse information and ECG information. As shown in FIG. 10, the steps of the algorithm may be illustrated as follows:

Step 1001: the pulse information and the ECG information may be received;

Step 1002: a noise result of the pulse information and a noise result of the ECG information may be calculated respectively by using one or more algorithms including algorithm A (1002-1), algorithm B (1002-2), algorithm C (1002-3). The algorithm A, the algorithm B, and the algorithm C may or may not be the same as that in FIGS. 7, 8, and 9.

Step 1003: a global noise result may be obtained based on one or more noise results of the three noise results calculated in step 1002.

Step 1004: a physiological sign of a living body may be calculated.

In step 1002, a plurality of combination modes may be used. For example, only the algorithm A, the algorithm B, or the algorithm C may be used, a combination of any two of the algorithm A, the algorithm B, and the algorithm C may be used, or all of the algorithm A, the algorithm B, and the algorithm C may be used.

In step 1003, a plurality of combination modes may be used. For example, any of the three noise results may be used, a combination of any two of the three noise results may be used, or all of the three noise results may be used.

In step 1004, the physiological sign of the living body may be calculated by one or more methods such as eliminating the noise result determined in step 1003, strengthening the noise result determined in step 1003, weakening the noise result determined in step 1003, etc. The physiological sign may include a blood pressure, a PR value, a blood oxygen saturation, a heart rate, a heart murmur, a bowel sound, a PH value, a creatinine content, a transferase content, a body temperature, a carcinoembryonic antigen content, or the like, or a combination thereof.

It should be noted that the steps, operations, or functions disclosed herein may be executed as shown in order, in parallel, or omitted in some cases. Similarly, the order of processing is not necessary to implement the features and advantages of the exemplary embodiments described herein, rather provided for illustration and description purposes. One or more of the steps, functions, or operations shown may be repeated according to a specific strategy used. In addition, the operations, functions, and/or steps may be represented in the figures and may be turned into codes in a computer-readable storage medium of a control system.

It should also be noted that the structures and configurations disclosed herein are essentially exemplary, and that these specific embodiments are not limited since variations are possible. The subject disclosed herein includes all structures and configurations as well as other features, functions, and/or all novel and non-obvious combinations and sub-combinations of the attributes disclosed herein.

The claims of the present application point out specifically novel and non-obvious specific combinations and sub-combinations. The claims may refer to "an" element or "first" element or its equivalence. Such claims are to be understood to include a combination of one or more such elements, rather than requiring or excluding two or more such elements. Other combinations and sub-combinations of the disclosed features, functions, elements and/or attributes may be claimed by modifying the claims of the present application or by proposing new claims in the present application or a related application. Such claims, whether they are broader, narrower, equivalent, or different in scope than the original claims, are to be considered as being included in the subject of the present disclosure.

What is claimed is:

1. A system for monitoring a physiological sign of a subject, comprising:
   a computer-readable storage medium storing a first set of instructions for processing data;
   at least one processor in communication with the computer-readable storage medium, wherein when executing the first set of instructions, the at least one processor is directed to:

receive a pulse related signal and an electrocardiograph (ECG) signal;

identify pulse peaks of the pulse related signal by a first technique and ECG peaks of the ECG signal by a second technique, the first technique being different from the second technique;

perform a matching operation between the pulse peaks and the ECG peaks;

identify one or more candidate noise peaks from the pulse peaks of the physiological information pulse related signal based on the matching operation;

process the pulse related signal by reducing or removing the one or more candidate noise peaks; and monitor a physiological sign of a subject based on the processed pulse related signal and the ECG signal.

2. The system of claim 1, wherein the first technique includes a PPG peak detection algorithm, and the second technique includes an ECG algorithm.

3. The system of claim 1, wherein to identify the one or more candidate noise peaks from the pulse peaks of the pulse related signal based on the matching operation, the at least one processor is directed to:

determine a pulse peak that is not matched with a corresponding ECG peak as a candidate noise peak.

4. The system of claim 1, wherein the system includes an I/O module configured to output and display the physiological sign.

5. The system of claim 1, wherein to process the pulse related signal by reducing or removing the one or more candidate noise peaks, the at least one processor is further directed to:

determine whether a noise reduction operation or a noise removal operation needs to be performed on the pulse related signal by: (1) determining one or more noise ratios corresponding to the one or more candidate noise peaks respectively; (2) if a count of noise peaks with noise ratios not less than 1 is greater than half of a count of the ECG peaks, or (3) if a count of noise peaks with noise ratios not less than 0.75 is greater than 0.75 times of the count of the waves identified based on the algorithm ECG peaks, or (4) if a count of noise peaks with noise ratios not less than 0.5 is greater than the count of the ECG peaks, determining that a noise reduction operation or a noise removal operation needs to be performed on the pulse related signal; and process the pulse related signal by reducing or removing the one or more candidate noise peaks in response to determining that a noise reduction operation or a noise removal operation needs to be performed on the pulse related signal.

6. The system of claim 5, wherein the noise ratio is a ratio of an amplitude value of a candidate noise peak to an average amplitude value of matched pulse peaks other than the one or more candidate noise peaks in the pulse related signal.

7. The system of claim 1, wherein the physiological sign comprises at least one of a heart rate, a blood pressure, oxygen saturation, a body temperature, a Heart Rate variability (HRV), or a Pulse Rate (PR) value.

8. A method for monitoring a physiological sign of a subject, comprising:

receiving a pulse related signal and an electrocardiograph (ECG) signal;

identifying pulse peaks of the pulse related signal by a first technique and ECG peaks of the ECG signal by a second technique respectively, the first technique being different from the second technique;

performing a matching operation between the pulse peaks and the ECG peaks;

identifying one or more candidate noise peaks from the pulse peaks of the puke related signal based on the matching operation;

processing the pulse related signal by reducing or removing the one or more candidate noise peaks; and monitoring a physiological sign of a subject based on the processed puke related signal and the ECG signal.

9. The method of claim 8, wherein the first technique includes a PPG peak detection algorithm, and the second technique includes an ECG algorithm.

10. The method of claim 8, wherein the identifying the one or more candidate noise peaks from the pulse peaks of the pulse related signal based on the matching operation includes:

determining a pulse peak that is not matched with a corresponding ECG peak as a candidate noise peak.

11. The method of claim 8, wherein the processing the pulse related signal by reducing or removing the one or more candidate noise peaks includes:

determining whether a noise reduction operation or a noise removal operation needs to be performed on the pulse related signal by: (1) determining one or more noise ratios corresponding to the one or more candidate noise peaks respectively; (2) if a count of noise peaks with noise ratios not less than 1 is greater than half a count of the ECG peaks, or (3) if a count of noise peaks with noise ratios not less than 0.75 is greater than 0.75 times of the count of the ECG peaks, or (4) if a count of noise peaks with noise ratios not less than 0.5 is greater than the count of the the ECG peaks, determining that a noise reduction operation or a noise removal operation needs to be performed on the pulse related signal; and processing the pulse related signal by reducing or removing the one or more candidate noise peaks in response to determining that a noise reduction operation or a noise removal operation needs to be performed on the pulse related signal.

12. The method of claim 11, wherein the noise ratio is a ratio of an amplitude value of a candidate noise peak to an average amplitude value of pulse peaks other than the one or more candidate noise peaks in the pulse related signal.

13. The method of claim 8, wherein the physiological sign comprises at least one of a heart rate, a blood pressure, oxygen saturation, a body temperature, a Heart Rate variability (HRV), or a Pulse Rate (PR) value.

14. The method of claim 8, wherein the method further includes:

outputting and displaying the physiological sign via an I/O module.

* * * * *